United States Patent
Henne et al.

(10) Patent No.: US 11,653,927 B2
(45) Date of Patent: May 23, 2023

(54) VAPOR ABLATION TREATMENT OF OBSTRUCTIVE LUNG DISEASE

(71) Applicant: Uptake Medical Technology Inc., Seattle, WA (US)

(72) Inventors: Erik Henne, Seattle, WA (US); Robert L. Barry, Kirkland, WA (US); Thomas M. Keast, Sunnyvale, CA (US)

(73) Assignee: Uptake Medical Technology Inc., Seattle, WA (US)

(*) Notice: Subject to any disclaimer, the term of this patent is extended or adjusted under 35 U.S.C. 154(b) by 577 days.

(21) Appl. No.: 16/789,097

(22) Filed: Feb. 12, 2020

(65) Prior Publication Data
US 2020/0261097 A1    Aug. 20, 2020

Related U.S. Application Data

(60) Provisional application No. 62/807,014, filed on Feb. 18, 2019.

(51) Int. Cl.
*A61B 17/12*     (2006.01)
*A61B 17/24*     (2006.01)
(Continued)

(52) U.S. Cl.
CPC .. *A61B 17/12104* (2013.01); *A61B 17/12136* (2013.01); *A61B 2017/00292* (2013.01); *A61B 2017/00557* (2013.01); *A61B 2017/242* (2013.01); *A61B 2018/00577* (2013.01); *A61B 2018/00625* (2013.01)

(58) Field of Classification Search
CPC .... A61B 2017/00292; A61B 2017/242; A61B 2018/00577; A61B 2018/00625; A61B 2018/00541; A61B 2018/00726
See application file for complete search history.

(56) References Cited

U.S. PATENT DOCUMENTS

| 408,899 A | 8/1889 | Small |
| 1,719,750 A | 7/1929 | Bridge et al. |

(Continued)

FOREIGN PATENT DOCUMENTS

| AU | 721086 B2 | 6/2000 |
| EP | 1003582 B1 | 2/2003 |

(Continued)

OTHER PUBLICATIONS

Becker, et al.; Lung volumes before and after lung volume reduction surgery; Am J Respir Crit Care Med; vol. 157; pp. 1593-1599; (1998) Oct. 28, 1997.

(Continued)

*Primary Examiner* — Sarah A Simpson
(74) *Attorney, Agent, or Firm* — Richard Batt

(57) ABSTRACT

A treatment of obstructive lung disease includes aiming a condensable vapor towards the airway wall, causing a band-shaped lesion to grow to a depth into the airway wall. Ablation parameters are set to control the depth of the band-shaped lesion to encompass the epithelial layer and exclude the smooth muscle layer of the airway. A wide variety of configurations of the vapor delivery are described to create ablation patterns in the airways of the patient with particular emphasis on treating chronic bronchitis.

23 Claims, 10 Drawing Sheets

Figure 2A:
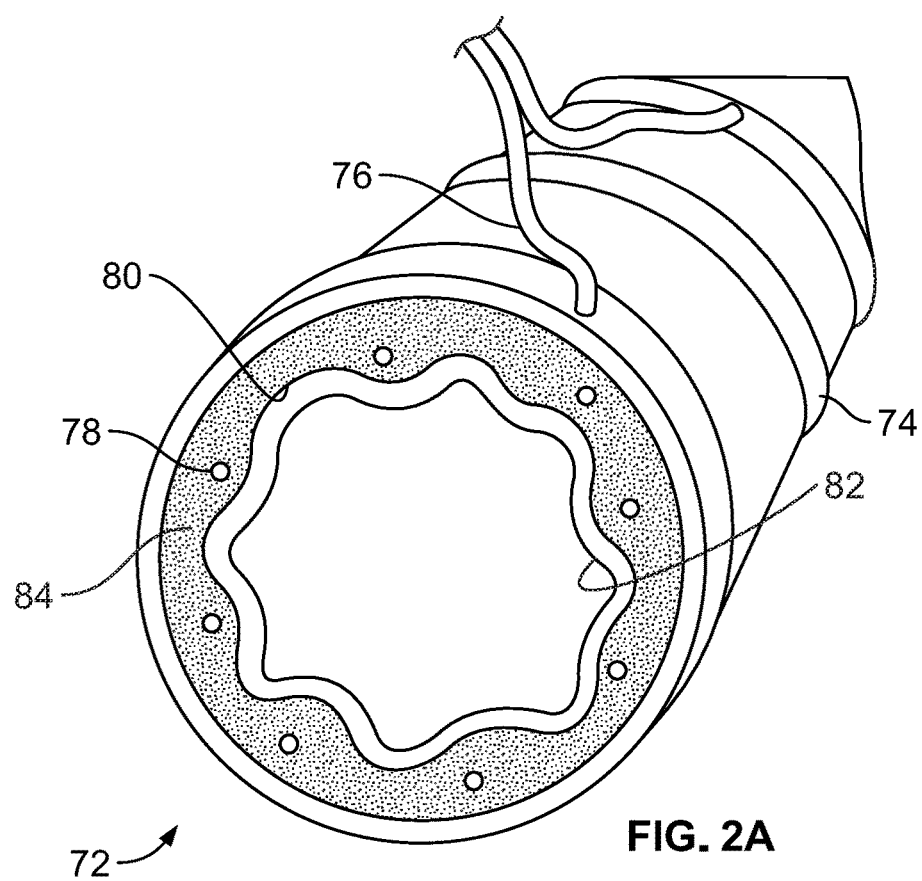
Figure 2B:
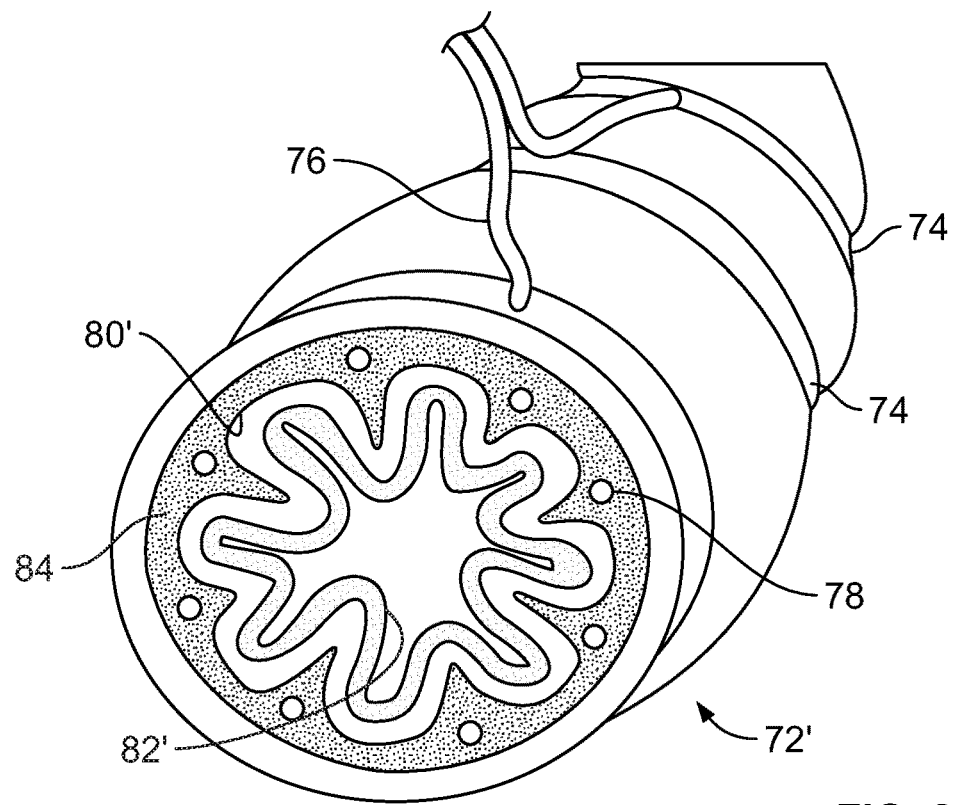

(51) Int. Cl.
*A61B 18/00* (2006.01)
*A61B 17/00* (2006.01)

(56) References Cited

U.S. PATENT DOCUMENTS

| | | |
|---|---|---|
| 3,507,283 A | 4/1970 | Thomas, Jr. |
| 3,880,168 A | 4/1975 | Berman |
| 4,026,285 A | 5/1977 | Jackson |
| 4,713,060 A | 12/1987 | Riuli |
| 4,773,410 A | 9/1988 | Blackmer et al. |
| 4,793,352 A | 12/1988 | Eichenlaub |
| 4,915,113 A | 4/1990 | Holman |
| 4,950,266 A | 8/1990 | Sinofsky |
| 5,006,119 A | 4/1991 | Acker et al. |
| 5,011,566 A | 4/1991 | Hoffman |
| 5,084,043 A | 1/1992 | Hertzmann et al. |
| 5,112,328 A | 5/1992 | Taboada et al. |
| 5,158,536 A | 10/1992 | Michael et al. |
| 5,263,951 A | 11/1993 | Spears et al. |
| 5,331,947 A | 7/1994 | Shturman |
| 5,334,190 A | 8/1994 | Seiler |
| 5,348,551 A | 9/1994 | Spears et al. |
| 5,352,512 A | 10/1994 | Hoffman |
| 5,424,620 A | 6/1995 | Cheon et al. |
| 5,462,521 A | 10/1995 | Brucker et al. |
| 5,500,012 A | 3/1996 | Brucker et al. |
| 5,503,638 A | 4/1996 | Cooper et al. |
| 5,524,620 A | 6/1996 | Rosenschein |
| 5,529,076 A | 6/1996 | Schachar |
| 5,549,628 A | 8/1996 | Cooper et al. |
| 5,562,608 A | 10/1996 | Michael et al. |
| 5,575,803 A | 11/1996 | Cooper et al. |
| 5,591,157 A | 1/1997 | Hennings et al. |
| 5,620,440 A | 4/1997 | Heckele et al. |
| 5,695,507 A | 12/1997 | Auth et al. |
| 5,735,811 A | 4/1998 | Brisken |
| 5,752,965 A | 5/1998 | Francis et al. |
| 5,755,753 A | 5/1998 | Knowlton |
| 5,779,642 A | 7/1998 | Nightengale |
| 5,782,914 A | 7/1998 | Schankereli |
| 5,800,482 A | 9/1998 | Pomeranz et al. |
| 5,824,703 A | 10/1998 | Clark, Jr. |
| 5,827,268 A | 10/1998 | Laufer |
| 5,913,856 A | 6/1999 | Chia et al. |
| 5,957,919 A | 9/1999 | Laufer |
| 5,964,752 A | 10/1999 | Stone |
| 5,972,026 A | 10/1999 | Laufer et al. |
| 5,986,662 A | 11/1999 | Argiro et al. |
| 5,989,445 A | 11/1999 | Wise et al. |
| 6,032,077 A | 2/2000 | Pomeranz |
| 6,053,909 A | 4/2000 | Shadduck |
| 6,059,011 A | 5/2000 | Giolo |
| 6,083,255 A | 7/2000 | Laufer et al. |
| 6,099,251 A | 8/2000 | Lafleur |
| 6,102,037 A | 8/2000 | Koch |
| 6,113,722 A | 9/2000 | Hoffman et al. |
| 6,130,671 A | 10/2000 | Argiro |
| 6,131,570 A | 10/2000 | Schuster et al. |
| 6,139,571 A | 10/2000 | Fuller et al. |
| 6,156,036 A | 12/2000 | Sussman et al. |
| 6,162,232 A | 12/2000 | Shadduck |
| 6,179,805 B1 | 1/2001 | Sussman et al. |
| 6,194,066 B1 | 2/2001 | Hoffman |
| 6,200,333 B1 | 3/2001 | Laufer |
| 6,210,404 B1 | 4/2001 | Shadduck |
| 6,219,059 B1 | 4/2001 | Argiro |
| 6,273,907 B1 | 8/2001 | Laufer |
| 6,283,988 B1 | 9/2001 | Laufer et al. |
| 6,283,989 B1 | 9/2001 | Laufer et al. |
| 6,299,633 B1 | 10/2001 | Laufer |
| 6,300,150 B1 | 10/2001 | Venkatasubramanian |
| 6,312,474 B1 | 11/2001 | Francis et al. |
| 6,327,505 B1 | 12/2001 | Medhkour et al. |
| 6,394,949 B1 | 5/2002 | Crowley et al. |
| 6,398,759 B1 | 6/2002 | Sussman et al. |
| 6,398,775 B1 | 6/2002 | Perkins et al. |
| 6,409,723 B1 | 6/2002 | Edwards |
| 6,411,852 B1 | 6/2002 | Danek et al. |
| 6,458,231 B1 | 10/2002 | Wapner et al. |
| 6,468,313 B1 | 10/2002 | Claeson et al. |
| 6,488,673 B1 | 12/2002 | Laufer et al. |
| 6,493,589 B1 | 12/2002 | Medhkour et al. |
| 6,508,816 B2 | 1/2003 | Shadduck |
| 6,527,761 B1 | 3/2003 | Soltesz et al. |
| 6,575,929 B2 | 6/2003 | Sussman et al. |
| 6,579,270 B2 | 6/2003 | Sussman et al. |
| 6,585,639 B1 | 7/2003 | Kotmel et al. |
| 6,588,613 B1 | 7/2003 | Pechenik et al. |
| 6,589,201 B1 | 7/2003 | Sussman et al. |
| 6,592,594 B2 | 7/2003 | Rimbaugh et al. |
| 6,599,311 B1 | 7/2003 | Biggs et al. |
| 6,610,043 B1 | 8/2003 | Ingenito |
| 6,629,951 B2 | 10/2003 | Laufer et al. |
| 6,652,594 B2 | 11/2003 | Francis et al. |
| 6,653,525 B2 | 11/2003 | Ingenito et al. |
| 6,669,694 B2 | 12/2003 | Shadduck |
| 6,676,628 B2 | 1/2004 | Sussman et al. |
| 6,679,264 B1 | 1/2004 | Deem et al. |
| 6,682,520 B2 | 1/2004 | Ingenito |
| 6,692,494 B1 | 2/2004 | Cooper et al. |
| 6,712,812 B2 | 3/2004 | Roschak et al. |
| 6,719,738 B2 | 4/2004 | Mehier |
| 6,755,794 B2 | 6/2004 | Soukup |
| 6,770,070 B1 | 8/2004 | Balbierz |
| 6,776,765 B2 | 8/2004 | Soukup et al. |
| 6,860,847 B2 | 3/2005 | Alferness et al. |
| 6,885,888 B2 | 4/2005 | Rezai |
| 6,901,927 B2 | 6/2005 | Deem et al. |
| 6,904,909 B2 | 6/2005 | Deem et al. |
| 6,907,881 B2 | 6/2005 | Suki et al. |
| 6,911,028 B2 | 6/2005 | Shadduck |
| 6,986,769 B2 | 1/2006 | Nelson et al. |
| 6,997,189 B2 | 2/2006 | Biggs et al. |
| 7,022,088 B2 | 4/2006 | Keast et al. |
| 7,027,869 B2 | 4/2006 | Danek et al. |
| 7,031,504 B1 | 4/2006 | Argiro et al. |
| 7,083,612 B2 | 8/2006 | Littrup et al. |
| 7,128,748 B2 | 10/2006 | Mooradian et al. |
| 7,136,064 B2 | 11/2006 | Zuiderveld |
| 7,144,402 B2 | 12/2006 | Kuester et al. |
| 7,144,588 B2 | 12/2006 | Nicholas et al. |
| 7,174,644 B2 | 2/2007 | Critelli et al. |
| 7,175,644 B2 | 2/2007 | Cooper et al. |
| 7,192,400 B2 | 3/2007 | Campbell et al. |
| 7,198,635 B2 | 4/2007 | Danaek et al. |
| 7,233,820 B2 | 6/2007 | Gilboa |
| 7,235,070 B2 | 6/2007 | Vanney |
| 7,335,195 B2 | 2/2008 | Mehier |
| 7,347,859 B2 | 3/2008 | Garabedian et al. |
| 7,412,977 B2 | 8/2008 | Fields et al. |
| 7,422,563 B2 | 9/2008 | Roschak et al. |
| 7,422,584 B2 | 9/2008 | Loomas et al. |
| 7,425,212 B1 | 9/2008 | Danek et al. |
| 7,462,162 B2 | 12/2008 | Phan et al. |
| 7,628,789 B2 | 12/2009 | Soltesz et al. |
| 7,708,712 B2 | 5/2010 | Phan et al. |
| 7,740,017 B2 | 6/2010 | Danek et al. |
| 7,756,563 B2 | 7/2010 | Higgins et al. |
| 7,778,704 B2 | 8/2010 | Rezai et al. |
| 7,815,590 B2 | 10/2010 | Cooper |
| 7,819,908 B2 | 10/2010 | Ingenito |
| 7,889,905 B2 | 2/2011 | Higgins et al. |
| 7,906,124 B2 | 3/2011 | Laufer et al. |
| 7,913,698 B2 | 3/2011 | Barry et al. |
| 7,985,187 B2 | 7/2011 | Wibowo et al. |
| 7,993,323 B2 | 8/2011 | Barry et al. |
| 8,002,740 B2 | 8/2011 | Willink et al. |
| 8,088,127 B2 | 1/2012 | Mayse et al. |
| 8,172,827 B2 | 5/2012 | Deem et al. |
| 8,187,269 B2 | 5/2012 | Shadduck et al. |
| 8,251,070 B2 | 8/2012 | Danek et al. |
| 8,292,882 B2 | 10/2012 | Danek et al. |
| 8,322,335 B2 | 12/2012 | Barry et al. |
| 8,409,167 B2 | 4/2013 | Roschak |

(56) References Cited

U.S. PATENT DOCUMENTS

| | | |
|---|---|---|
| 8,444,636 B2 | 5/2013 | Shadduck et al. |
| 8,585,645 B2 | 11/2013 | Barry et al. |
| 8,608,724 B2 | 12/2013 | Roschak |
| 8,628,495 B2 | 1/2014 | Horton et al. |
| 8,709,034 B2 | 4/2014 | Keast et al. |
| 8,734,380 B2 | 5/2014 | Barry et al. |
| 8,784,400 B2 | 7/2014 | Roschak |
| 8,858,549 B2 | 10/2014 | Shadduck et al. |
| 8,900,223 B2 | 12/2014 | Shadduck |
| 9,037,215 B2 | 5/2015 | Higgins et al. |
| 9,050,076 B2 | 6/2015 | Barry et al. |
| 9,133,858 B2 | 9/2015 | Macchia et al. |
| 9,265,468 B2 | 2/2016 | Rai et al. |
| 9,913,969 B2 | 3/2018 | Roschak |
| 10,064,697 B2 | 9/2018 | Sharma et al. |
| 2002/0077516 A1 | 6/2002 | Flanigan |
| 2002/0111386 A1 | 8/2002 | Michael et al. |
| 2002/0112723 A1 | 8/2002 | Schuster et al. |
| 2002/0177846 A1 | 11/2002 | Mulier et al. |
| 2003/0055331 A1 | 3/2003 | Kotmel et al. |
| 2003/0099279 A1 | 5/2003 | Venkatasubramanian et al. |
| 2003/0181922 A1 | 9/2003 | Alferness |
| 2003/0233099 A1 | 12/2003 | Danaek et al. |
| 2004/0031494 A1 | 2/2004 | Danek et al. |
| 2004/0038868 A1 | 2/2004 | Ingenito |
| 2004/0047855 A1 | 3/2004 | Ingenito |
| 2004/0055606 A1 | 3/2004 | Hendricksen et al. |
| 2004/0068306 A1 | 4/2004 | Shadduck |
| 2004/0199226 A1 | 10/2004 | Shadduck |
| 2004/0200484 A1 | 10/2004 | Springmeyer |
| 2004/0244803 A1 | 12/2004 | Tanaka |
| 2005/0016530 A1 | 1/2005 | Mccutcheon et al. |
| 2005/0066974 A1 | 3/2005 | Fields et al. |
| 2005/0166925 A1 | 8/2005 | Wilson et al. |
| 2005/0171396 A1 | 8/2005 | Pankratov et al. |
| 2005/0171582 A1 | 8/2005 | Matlock |
| 2005/0203483 A1 | 9/2005 | Perkins et al. |
| 2005/0215991 A1 | 9/2005 | Altman et al. |
| 2005/0222485 A1 | 10/2005 | Shaw et al. |
| 2006/0004400 A1 | 1/2006 | Mcgurk et al. |
| 2006/0047291 A1 | 3/2006 | Barry |
| 2006/0100619 A1 | 5/2006 | Mcclurken et al. |
| 2006/0130830 A1 | 6/2006 | Barry |
| 2006/0135955 A1 | 6/2006 | Shadduck |
| 2006/0162731 A1 | 7/2006 | Wondka et al. |
| 2006/0200076 A1 | 9/2006 | Gonzalez et al. |
| 2006/0224154 A1 | 10/2006 | Shadduck et al. |
| 2007/0032785 A1 | 2/2007 | Diederich et al. |
| 2007/0036417 A1 | 2/2007 | Argiro et al. |
| 2007/0068530 A1 | 3/2007 | Pacey |
| 2007/0091087 A1 | 4/2007 | Zuiderveld |
| 2007/0092864 A1 | 4/2007 | Reinhardt et al. |
| 2007/0102011 A1 | 5/2007 | Danek et al. |
| 2007/0106292 A1 | 5/2007 | Kaplan et al. |
| 2007/0109299 A1 | 5/2007 | Peterson |
| 2007/0112349 A1 | 5/2007 | Danek et al. |
| 2007/0118184 A1 | 5/2007 | Danek et al. |
| 2007/0137646 A1 | 6/2007 | Weinstein et al. |
| 2007/0293853 A1 | 12/2007 | Truckai et al. |
| 2008/0033493 A1 | 2/2008 | Deckman et al. |
| 2008/0132826 A1 | 6/2008 | Shadduck et al. |
| 2008/0249439 A1 | 10/2008 | Tracey et al. |
| 2009/0018538 A1 | 1/2009 | Webster et al. |
| 2009/0043301 A1 | 2/2009 | Jarrard et al. |
| 2009/0118538 A1 | 5/2009 | Pizzocaro et al. |
| 2009/0138001 A1 | 5/2009 | Barry et al. |
| 2009/0149846 A1 | 6/2009 | Hoey et al. |
| 2009/0149897 A1 | 6/2009 | Dacey, Jr. et al. |
| 2009/0156895 A1 | 6/2009 | Higgins et al. |
| 2009/0192508 A1 | 7/2009 | Laufer et al. |
| 2009/0216220 A1 | 8/2009 | Hoey et al. |
| 2009/0301483 A1 | 12/2009 | Barry et al. |
| 2009/0306640 A1 | 12/2009 | Glaze et al. |
| 2009/0306644 A1 | 12/2009 | Mayse et al. |
| 2009/0312753 A1 | 12/2009 | Shadduck |
| 2010/0094270 A1 | 4/2010 | Sharma |
| 2010/0204688 A1 | 8/2010 | Hoey et al. |
| 2010/0256714 A1 | 10/2010 | Springmeyer |
| 2010/0262133 A1 | 10/2010 | Hoey et al. |
| 2010/0310146 A1 | 12/2010 | Higgins et al. |
| 2011/0077628 A1 | 3/2011 | Hoey et al. |
| 2011/0118725 A1 | 5/2011 | Mayse et al. |
| 2011/0160648 A1 | 6/2011 | Hoey |
| 2011/0172654 A1 | 7/2011 | Barry et al. |
| 2011/0257644 A1 | 10/2011 | Barry et al. |
| 2011/0270031 A1 | 11/2011 | Frazier et al. |
| 2011/0301587 A1 | 12/2011 | Deem et al. |
| 2011/0319958 A1 | 12/2011 | Simon et al. |
| 2012/0016363 A1 | 1/2012 | Mayse et al. |
| 2012/0016364 A1 | 1/2012 | Mayse et al. |
| 2012/0289776 A1 | 11/2012 | Keast et al. |
| 2013/0006231 A1 | 1/2013 | Sharma et al. |
| 2013/0267939 A1 | 10/2013 | Barry et al. |
| 2013/0324987 A1 | 12/2013 | Leung et al. |
| 2014/0025057 A1 | 1/2014 | Hoey et al. |
| 2014/0275952 A1 | 9/2014 | Monroe et al. |
| 2014/0276713 A1 | 9/2014 | Hoey et al. |
| 2015/0094607 A1 | 4/2015 | Barry et al. |
| 2015/0230852 A1 | 8/2015 | Barry et al. |
| 2016/0180529 A1 | 6/2016 | Rai et al. |
| 2016/0220297 A1 | 8/2016 | Kroon et al. |
| 2016/0287307 A1 | 10/2016 | Clark et al. |
| 2016/0310200 A1 | 10/2016 | Wang |
| 2016/0354140 A1* | 12/2016 | Sharma ............... A61B 18/04 |
| 2016/0374710 A1 | 12/2016 | Sinelnikov et al. |
| 2017/0172640 A1 | 6/2017 | Henne |
| 2018/0036084 A1 | 2/2018 | Krimsky |
| 2018/0318002 A1 | 11/2018 | Barry et al. |
| 2019/0069948 A1 | 3/2019 | Herth et al. |
| 2019/0343579 A1 | 11/2019 | Tandri et al. |

FOREIGN PATENT DOCUMENTS

| | | |
|---|---|---|
| EP | 1143864 B1 | 2/2004 |
| EP | 1173103 B1 | 10/2005 |
| EP | 1326549 B1 | 12/2005 |
| EP | 1326548 B1 | 1/2006 |
| EP | 1485033 B1 | 8/2009 |
| WO | 0011927 A2 | 3/2000 |
| WO | 0102042 A1 | 1/2001 |
| WO | 02069821 A1 | 9/2002 |
| WO | 03070302 A1 | 8/2003 |
| WO | 03086498 A2 | 10/2003 |
| WO | 2005025635 A2 | 3/2005 |
| WO | 2005102175 A2 | 11/2005 |
| WO | 2006003665 A2 | 1/2006 |
| WO | 2006052940 A2 | 5/2006 |
| WO | 2006053308 A2 | 5/2006 |
| WO | 2006053309 A2 | 5/2006 |
| WO | 2006080015 A2 | 8/2006 |
| WO | 2006116198 A2 | 11/2006 |
| WO | 2008051706 A2 | 5/2008 |
| WO | 2009009236 A1 | 1/2009 |
| WO | 2009009398 A1 | 1/2009 |
| WO | 2009015278 A1 | 1/2009 |
| WO | 2009137819 A1 | 11/2009 |
| WO | 2010042461 A1 | 4/2010 |
| WO | 2011056684 A2 | 5/2011 |
| WO | 2011060200 A1 | 5/2011 |
| WO | 2011060201 A1 | 5/2011 |
| WO | 2011127216 A2 | 10/2011 |

OTHER PUBLICATIONS

Blacker, G. F.; Vaporization of the uterus; J. of Obstetrics and Gynaecology; vol. 33; pp. 488-511; 1902.

Carpenter III et al.; Comparison of endoscopic cryosurgery and electrocoagulation of bronchi; Trans. Amer. Acad. Opth.; vol. 84; No. 1; pp. ORL-313-ORL-323; Jan. 1977.

Clinical trials.gov.; Study of the AeriSeal System for Hyperinflation Reduction in Emphysema; 4 pages; Nov. 5, 2014; retrieved from the internet (http://clinicaltrials.gov/show/NCT01449292).

(56) References Cited

OTHER PUBLICATIONS

Coda, et al., "Effects of pulmonary reventilation on gas exchange after cryolytic disobstruction of endobronchial tumors," Minerva Medical, vol. 72, pp. 1627-1631, Jun. 1981 (w/ Eng. Trans.).
Cox et al., "Bronchial Thermoplasty for Asthma." American Journal of Respiratory Critical Care Medicine 173: 965-969 (2006).
Delaunois; Anatomy and physiology of collateral respiratory pathways; Eur. Respir. J.; 2(9); pp. 893-904; Oct. 1989.
Eyal et al.; The acute effect of pulmonary burns on lung mechanics and gas exchange in the rabbit; Br. J. Anaesth.; vol. 47; pp. 546-552; (year of publication is sufficiently earlier than the effective U.S. filing date and any foreign priority date) 1975.
Ferlay et al.; GLOBOCAN 2008 v1.2, Cancer Incidence and Mortality Worldwide: IARC CancerBase No. 10 [internet]; 16 pages; retrieved from the Internet (http://www.iarc.fr/en/media-centre/iarcnews/2010/GLOBOCAN2008.pdf); Lyon, France: International Agency for Research on Cancer; Jun. 1, 2010.
Fishman et al., A randomized trial comparing lung-volume-reduction surgery with medical therapy for severe emphysema, N Engl J Med, vol. 348, No. 21, pp. 2059-2073, May 22, 2003.
Goldberg et al.; Radiofrequency tissue ablation in the rabbit lung: Efficacy and complications; Acad. Radiol.; vol. 2; pp. 776-784; Sep. 1995.
Henne et al.; U.S. Appl. No. 14/957,433 entitled "Vapor treatment of lung nodules and tumors," filed Dec. 2, 2015.
Herth et al.; Efficacy predictors of lung volume reduction with zephyr valves in a european cohort; Eur. Respir. J.; 39(6); pp. 1334-1342; Jun. 2012.
Homasson, et al., "Bronchoscopic cryotherapy for airway strictures caused by tumors," Chest, vol. 90, No. 2, pp. 159-164, Aug. 1986.
Kang, Li, "Efficient optimal net surface detection for image segmentation—from theory to practice," M.Sc. Thesis, The University of Iowa, Dec. 2003.
Kinsella et al.; Quantitation of emphysema by computed tomography using a "densitymask" program and correlation with pulmonary function tests; Chest; 97(2); pp. 315-321; Feb. 1990.
Looga, R. U.; Mechanism of changes in the respiratory and cardiovascular reflexes from the lungs associated with intrapulmonary steam burns; Eng. Trans. from Byulleten Eksperimental noi Biologii I Meditsiny; vol. 61; No. 6; pp. 31-33; Jun. 1966.
Marasso, et al., "Cryosurgery in bronchoscopic treatment of tracheobronchial stenosis," Chest, vol. 103, No. 2, pp. 172-474, Feb. 1993.
Marasso, et al., "Radiofrequency resection of bronchial tumours in combination with cryotherapy: evaluation of a new technique," Thorax, vol. 53, pp. 106-109, (year of publication is sufficiently earlier than the effective U.S. filing date and any foreign priority date) 1998.
Mathur et al., Fiberoptic bronchoscopic cryotherapy in the management of tracheobronchial obstruction, Chest, vol. 110, No. 3, pp. 718-723, Sep. 1996.
Morice et al.; Endobrinchial argon plasma coagulation for treatment of hemotysis and neoplastic airway obstruction, Chest, vol. 119, No. 3, pp. 781-787, Mar. 2001.
Moritz et al.; The effects of inhaled heat on the air pasage and lungs; American Journal of Pathology; vol. XXI; pp. 311-331; (year of publication is sufficiently earlier than the effective U.S. filing date and any foreign priority date) 1944.
Moulding et al.; Preliminary studies for achieving transcervical oviduct occlusion by hot water or low-pressure steam; Advances in Planned Parenthood; vol. 12, No. 2; pp. 79-85; (year of publication is sufficiently earlier than the effective U.S. filing date and any foreign priority date) 1977.
National Lung Screening Trial Research Team; Reduced lung-cancer mortality with low-dose computed tomographic screening; N. Eng. J. Med.; 365(5); pp. 395-409; Aug. 4, 2011.
Pieter et al.; U.S. Appl. No. 15/013,748 entitled "Medical vapor generator," filed Feb. 2, 2016.
Pracht, Adam, "VIDA takes new approach," Iowa City Press-Citizen, Sep. 12, 2005.
Quin, Jacquelyn, "Use of neodymium yttrium aluminum garnet laser in long-term palliation of airway obstruction," Connecticut Medicine, vol. 59, No. 7, pp. 407-412, Jul. 1995.
Sciurba et al.; A randomized study of endobronchial valves for advanced emphysema; N. Eng. J. Med.; 363(13); pp. 1233-1244; Sep. 23, 2010.
Shah et al.; Collateral ventilation and selection of techniques for bronchoscopic lung volume reduction; Thorax; 67(4); pp. 285-286; Apr. 2012.
Slebos et al.; Bronchoscopic lung volume reduction coil treatment of patients with severe heterogeneous emphysema; Chest; 142(3); pp. 574-582; Sep. 2012.
Sutedja, et al.; Bronchoscopic treatment of lung tumors; Elsevier, Lung Cancer, 11, pp. 1-17, Jul. 1994.
Tschirren et al.; Intrathoracic airway trees: segmentation and airway morphology analysis from low-dose CT scans; IEEE Trans. Med. Imaging; vol. 24, No. 12; pp. 1529-1539; Dec. 2005.
Tschirren, Juerg; Segmentation, anatomical labeling, branchpoint matching, and quantitative analysis of human airway trees in volumetric CT images; Ph.D. Thesis; The University of Iowa; Aug. 2003.
Tschirren, Juerg; Segmentation, anatomical labeling, branchpoint matching, and quantitative analysis of human airway trees in volumetric CT images; Slides from Ph.D. defense; The University of Iowa; Jul. 10, 2003.
Van De Velde; Vapo-cauterization of the uterus; Amer. J. Med. Sci.; vol. CXVIII; (year of publication is sufficiently earlier than the effective U.S. filing date and any foreign priority date) 1899.
Vorre et al.; Morphology of tracheal scar after resection with CO2-laser and high-frequency cutting loop; Acta Otolaryngol (Stockh); vol. 107; pp. 307-312; (year of publication is sufficiently earlier than the effective U.S. filing date and any foreign priority date) 1989.

\* cited by examiner

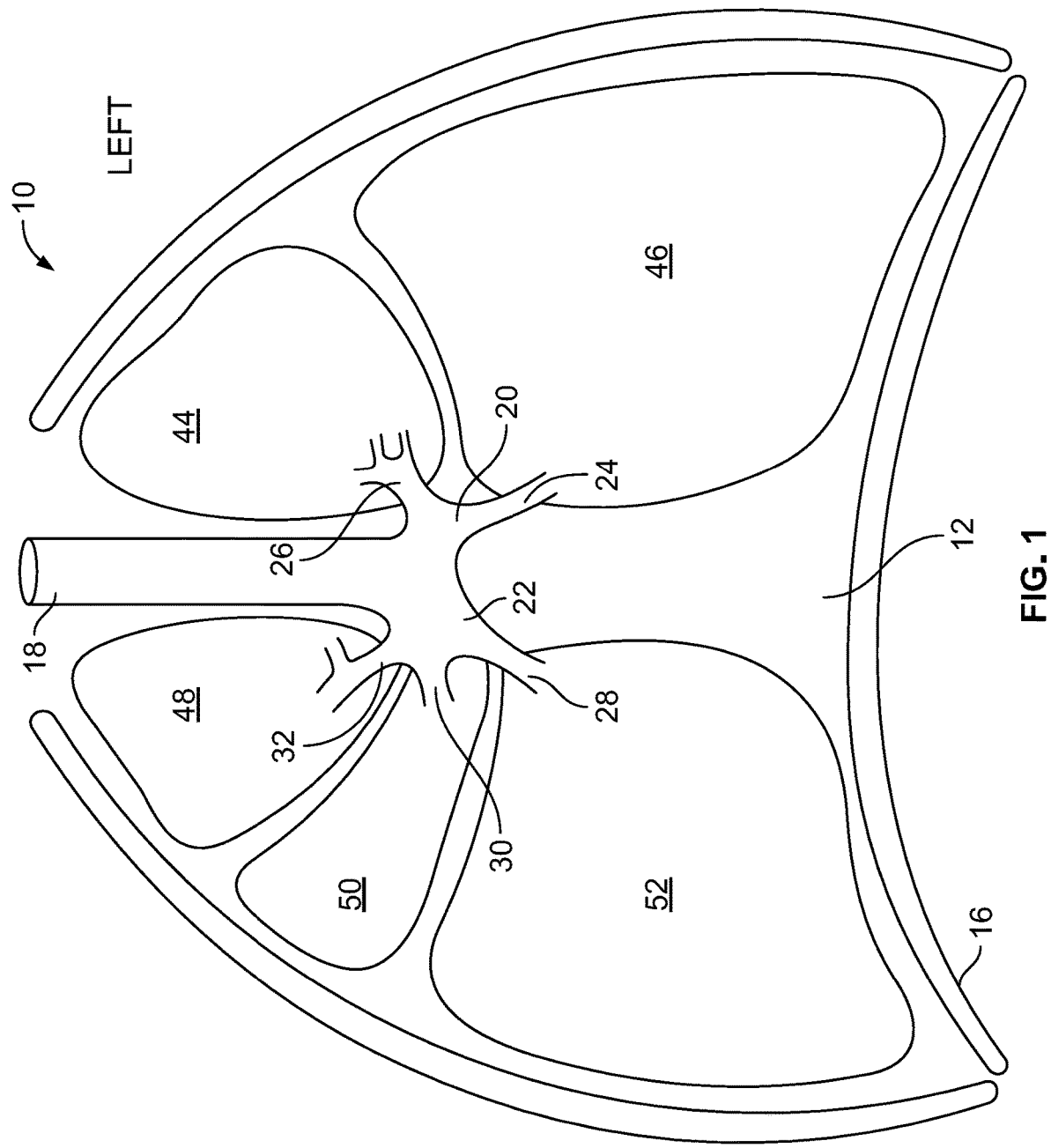

VAPOR ABLATION TREATMENT OF OBSTRUCTIVE LUNG DISEASE

CROSS-REFERENCE TO RELATED APPLICATIONS

This application claims priority to provisional application No. 62/807,014, filed Feb. 18, 2019, the entirety of which is herein incorporated by reference for all purposes.

BACKGROUND OF THE INVENTION

The present invention relates to medical methods for treating obstructive and or inflammatory lung disease, and more specifically to minimally invasive medical methods and apparatus' for ablating the inner wall of the airways to limit contraction and obstruction within airways.

Chronic obstructive pulmonary disease (COPD) and asthma are lung inflammatory diseases and affect many people. Each disease is characterized by limited airflow, and interferes with normal breathing. Although COPD includes a number of diseases including chronic bronchitis and emphysema, it is generally characterized by airflow obstruction. People with airflow obstruction may have a number of symptoms including smooth muscle contraction, chronic cough with excess sputum production, and general thickening of the airway wall, all of which result in obstruction of normal breathing.

Various approaches to treat COPD and asthma include pharmacological treatment and interventional treatments.

Pharmacological treatment is an approach applied to most patients. For example, it is not uncommon for a physician to administer an inhaled bronchodilator (short or long acting) once or twice daily to relax and temporarily open airways. However, the side effects of the pharmacological agents include: nausea and vomiting, diarrhea, palpitations, a rapid heartbeat, an irregular heartbeat, headaches, and problems sleeping (insomnia), all of which are undesirable.

On the other hand, some patients are candidates for interventional treatments.

A variety of thermal ablation based interventional treatments have been described as therapies to treat diseased airways.

U.S. Pat. No. 9,867,648 to Mulcahey, for example, describes a cryospray treatment of airway tissue. Spray cryotherapy is applied by spraying liquid nitrogen directly onto the bronchial wall with the intent of ablating superficial airway cells and initiating a regenerative effect on the bronchial wall.

Radiofrequency ablation techniques have also been described wherein energy is delivered to the airway wall in a variety of locations to ablate diseased tissue. An example of a RF based bronchial thermoplasty to reduce excess smooth muscle in the airway is described in U.S. Pat. No. 6,488,673 to Laufer et al. See also, the The Alair™ Bronchial Thermoplasty System (manufactured by Boston Scientific, Corporation, Marlborough, Mass., USA).

These thermal ablative technologies non-selectively ablate various layers of the airway wall, often undesirably ablating non-target tissues beyond the epithelium. As a consequence of damage to tissues beyond the therapeutic targets of the epithelium, an inflammatory cascade can be triggered, resulting in inflammation, which can lead to an exacerbation, and remodeling. As a result, the airway lumen can be further reduced. Thus, continued improvements in interventional procedures are needed which are more controlled, targeted to specific depths and structures that match the physiologic malady, while limiting the amount of inflammatory response and remodeling.

Accordingly, a system and method to treat obstructive lung and inflammatory disease that overcomes the above-mentioned challenges is still desirable.

SUMMARY OF THE INVENTION

The present invention includes an apparatus, system and method for ablating tissue for the treatment of obstructive lung or inflammatory diseases, and is particularly suitable for treatment of chronic bronchitis and asthma.

In embodiments, vapor is aimed directly towards the surface of the airway to create a ring-shaped ablation layer extending into the airway wall to a depth. In embodiments, the depth is controlled by ablation parameters to include only the epithelial layers and exclude other layers, such as smooth muscle. In embodiments, the depth of the ablation layer is controlled to be less than 1 mm, and more preferably between 0.3 and 0.7 mm, and most preferably about 0.4 to 0.6 mm.

In embodiments, an apparatus includes a distal section and at least one egress port along the distal section. The egress port aims condensable vapor at the airway wall.

In embodiments, the egress port is aimed such that the flowpath of the vapor is substantially perpendicular to the airway wall.

The configuration of the egress port(s) may vary. In embodiments, the distal section has a tubular shaped wall, and the egress port is disposed along the wall.

In embodiments, a plurality of egress ports are disposed circumferentially about the wall of the catheter. Additional egress ports or sets of egress ports may be located along a length of the catheter shaft.

In embodiments, the target region or section of the airway is isolated from a non-target section of the airway by at least one occluding member. The occluding member may be disposed proximal or distal to the egress port. In embodiments, occluding members are present on both the distal and proximal side of the egress port to define a volume or space which the vapor fills. In embodiments, the occluding members are expandable members such as an inflatable balloon.

In embodiments, the shaft may be operable with a proximal hub or handle to rotate or axially move the distal working section and egress port(s) relative to the isolation member. The hub may include a means to controllably advance and rotate the shaft carrying the egress ports relative to the balloon. In an embodiment, the means is a threaded shaft and mating grooves to allow incremental advancement of one of the components to the other.

In embodiments, a target region along the airway, and optionally an optimal route to the target region, is predetermined.

In embodiments, the vapor is delivered in pulses, and optionally, the heated vapor and a cooling gas is delivered in pulses according to an adjustable or varying duty cycle.

In embodiments, the duty cycle is adjusted based on the measured depth of the lesion.

In embodiments, the duty cycle commences at a first range, and is adjusted to a second range wherein the second range is less than the first range. In embodiments, the first range is from 70 to 100%, and the second range is under 50%.

In embodiments, the method further comprises visually monitoring the surface of the airway and computing a real-time hue change as the ablation layer is forming. In embodiments, the depth of ablation is controlled by halting the vapor delivery if the real-time hue change reaches a predetermined threshold hue change.

Still other descriptions, objects and advantages of the present invention will become apparent from the detailed description to follow, together with the accompanying drawings.

BRIEF DESCRIPTION OF THE DRAWINGS

FIG. 1 illustrates a human respiratory system;

FIGS. 2A, 2B illustrate an airway in the respiratory system in a normal and diseased state respectively;

FIG. 3 illustrates a bronchoscopic method for accessing and treating lung tissue;

FIG. 4A is a schematic diagram of an energy generator;

FIG. 4B is an illustration of a vapor generator;

FIG. 5 is an illustration of a vapor ablation catheter;

FIG. 6 is an enlarged view of a distal region of the vapor ablation catheter shown in FIG. 5 in an airway and applying vapor towards a target region of the airway;

FIG. 7A is an enlarged view of a distal region of another vapor ablation catheter in an airway and applying vapor towards the airway wall for treating obstructive and/or inflammatory lung disease;

FIG. 7B is an illustration of a hub of a vapor ablation catheter;

FIGS. 8A-8C are illustrations of vapor ablation catheters having differing balloon configurations;

FIG. 9 is an illustration of a vapor ablation catheter having a plurality of egress ports located together in the side wall of the shaft such that the vapor spray from adjacent egress ports overlap;

FIG. 10 is an illustration of a vapor ablation catheter having a plurality of egress ports spaced along the side wall of the shaft such that the vapor spray from adjacent egress ports does not overlap;

FIG. 11 is a treatment pattern including a plurality of band or ring-shaped lesions distributed about the lung; and FIG. 12 is a flowchart of a method for the treatment of obstructive lung and/or inflammatory disease.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms “a,” “an,” “said” and “the” include plural referents unless the context clearly dictates otherwise. It is further noted that the claims may be drafted to exclude any optional element. As such, this statement is intended to serve as antecedent basis for use of such exclusive terminology as “solely,” “only” and the like in connection with the recitation of claim elements, or use of a “negative” limitation.

Now, with reference to FIG. 1, pertinent anatomy is shown and described serving to facilitate understanding of the invention. Particularly, FIG. 1 illustrates a human respiratory system 10. The respiratory system 10 resides within the thorax 12 that occupies a space defined by the chest wall and the diaphragm 16. The human respiratory system 10 includes left lung lobes 44 and 46 and right lung lobes 48, 50, and 52.

The respiratory system 10 may be characterized by a tree-like structure formed of branched airways including the trachea 18; left and right main stem bronchus 20 and 22 (primary, or first generation) and lobar bronchial branches 24, 26, 28, 30, and 32 (second generation). Segmental and subsegmental branches further bifurcate off the lobar bronchial branches (third and fourth generation). Each bronchial branch and sub-branch communicates with a different portion of a lung lobe, either the entire lung lobe or a portion thereof.

FIGS. 2A, 2B illustrate cross sectional views of an airway in a normal state 72 and a diseased state 72', respectively. The diseased state may arise from, e.g., asthma, chronic bronchitis, or otherwise.

With reference to FIG. 2A, smooth muscles 74 are shown axially spaced along the airway in an uncontracted state. Nerves 76 communicate with the smooth muscles, and control movement of the smooth muscles 74. The nerves can affect the size or diameter of the airway passageway by causing the smooth muscles to constrict or expand. Blood vessels 78 serve to transport blood therethrough.

FIG. 2A also shows an epithelium layer 80 supported by basement membrane 84. The epithelium layer 80 is generally comprised of cells including goblet cells, columnar cells, and basal cells. The epithelium layer may have a depth ranging from 5 to 100 μm. Finally, a mucus layer 82 coats the epithelium layer.

FIG. 2B illustrates an airway 72' in a diseased state. The smooth muscles 74 are notably contracted. The epithelium layer 80' is substantially narrowed and the mucus layer 82' is increased and further narrows the airway.

Depending on the degree of the disease, the contracted and obstructed airways make breathing strained, if not impossible. Embodiments of the invention discussed herein provide methods and apparatus’ to treat obstructive and/or inflammatory diseases of the lung.

Bronchoscopy Approach

Figure 3:
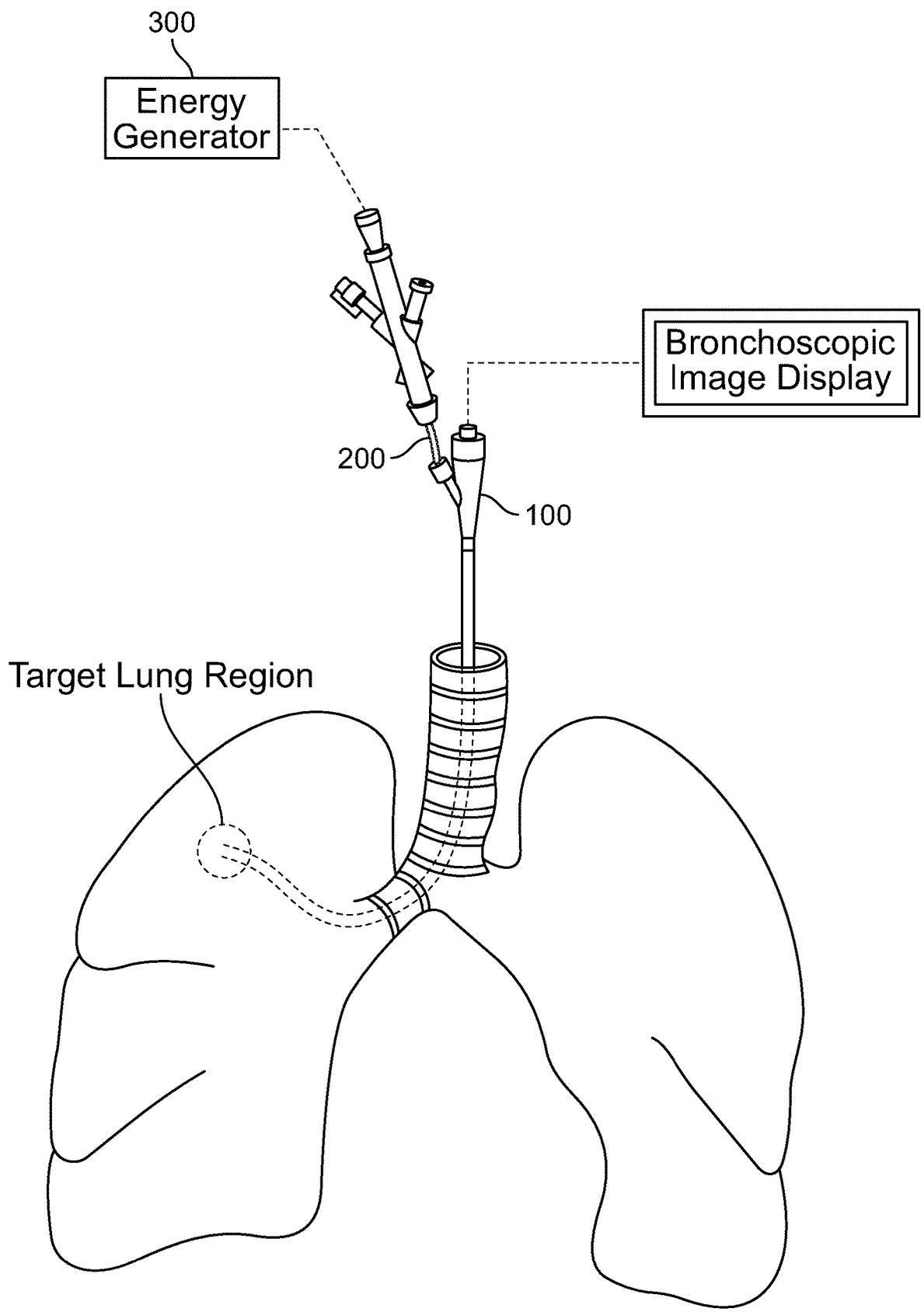

FIG. 3 illustrates a bronchoscopic procedure in accordance with some embodiments of the present invention. FIG. 3 shows a bronchoscope 100 having a working channel into which an energy delivery catheter 200 (or another tool) is inserted. Bronchoscope 100 is inserted into a patient's lungs while the proximal portion of the energy delivery catheter 200 remains outside of the patient. Energy delivery catheter 200 is adapted to operatively couple to an energy generator 300 as further discussed below. Examples of energy delivery catheters include, without limitation, a condensable vapor ablation catheter as described herein.

Energy Generator

Figure 4A:
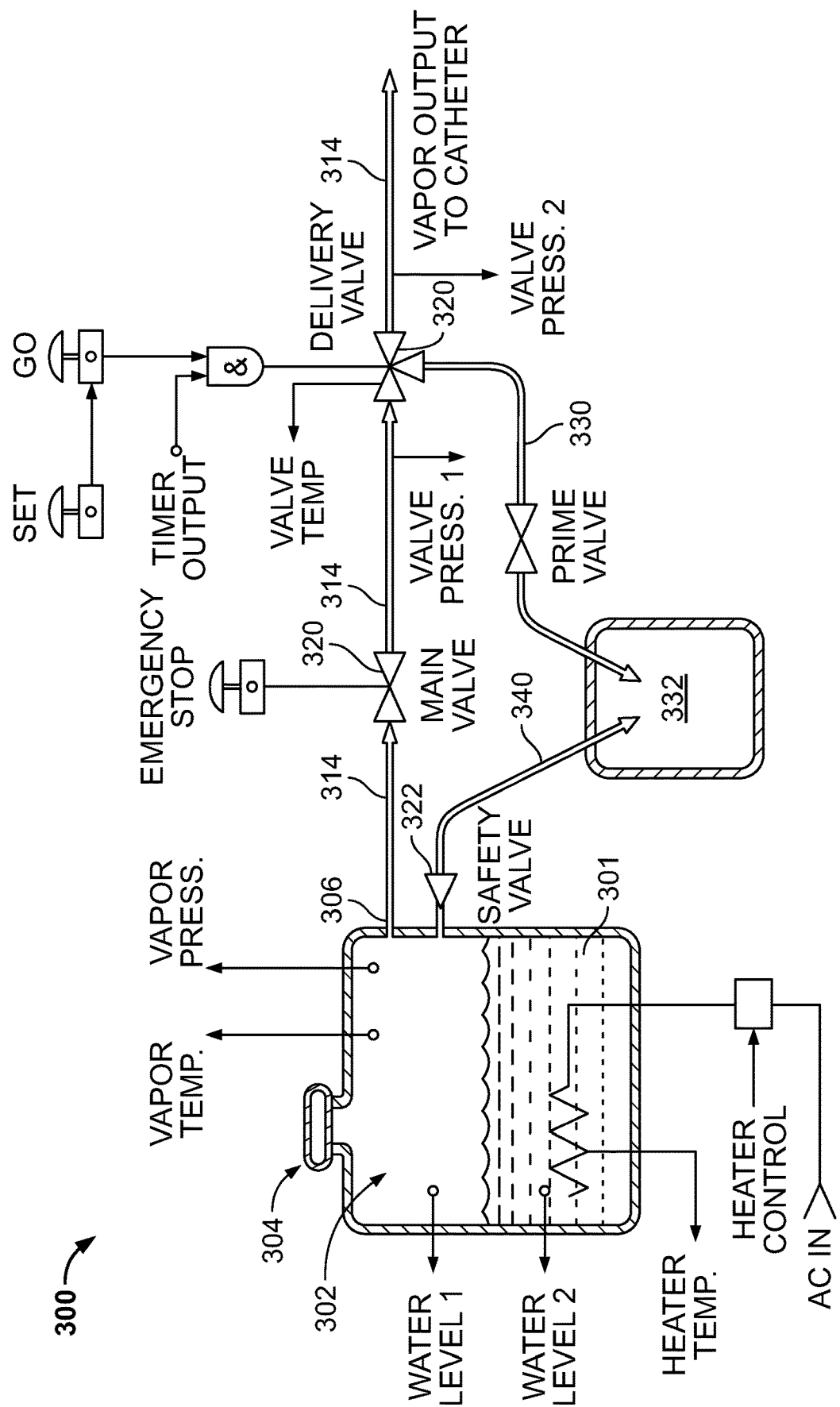

FIG. 4A is a schematic diagram of an energy generator 300 configured as a vapor generator. In embodiments, vapor generator is configured to deliver a controlled dose of vapor to one or more target lung tissues. Vapor generator 300 is adapted to convert a biocompatible liquid 301 (e.g. saline, sterile water or other biocompatible liquid), into a wet or dry vapor, which is then delivered to one or more target tissues. A wet vapor refers to a vapor that contains vaporous forms of the liquid as well as a non-negligible proportion of minute liquid droplets carried over with and held in suspension in the vapor. A dry vapor refers to a vapor that contains little or no liquid droplets. In general, vapor generator 300 is configured to have a liquid capacity between about 5 and 1000 cc and configured to generate a vapor having a pressure between about 5-100 psig and temperatures between about 100-175° C.

In embodiments, vapor generator 300 is configured as a self-contained, medical-grade generator unit comprising at least a vaporizing unit 302, a fluid inlet 304, and a vapor outlet 306. The vaporizing unit 302 comprises a fluid chamber for containing a fluid 301, preferably a biocompatible, sterile fluid, in a liquid state. In embodiments, vapor outlet 306 is coupled to one or more pipes or tubes 314, which in turn are placed in fluid communication with an energy delivery catheter 200. Vapor flow from vapor generator 300 to a catheter (and specifically a vapor lumen of said catheter) is depicted as a vapor flow circuit 314 wherein flow of the vapor in circuit 314 is indicated by arrows 314 in FIG. 4. In a preferred embodiment, vapor generator is configured to deliver a repeatable dose of vapor to the energy delivery catheter. Suitable doses of vapor range from 100 to 1000 calories.

Vaporizer unit 302 is configured to heat and vaporize a liquid contained therein. Other components can be incorporated into the biocompatible liquid 301 or mixed into the vapor. For example, these components can be used to control perioperative and/or post procedural pain, enhance tissue fibrosis, and/or control infection. Other constituents, for the purpose of regulating vapor temperatures and thus control extent and speed of tissue heating, can be incorporated; for example, in one implementation, carbon dioxide, helium, other noble gases can be mixed with the vapor to decrease vapor temperatures.

Vaporizing unit 302 is also shown having a fluid inlet 304 to allow liquid 301 to be added to the fluid chamber as needed. Fluid chamber can be configured to accommodate or vaporize sufficient liquid as needed to apply vapor to one or more target tissues. Liquid in vaporizing unit 302 is heated and vaporized and the vapor flows into vapor outlet 306. A number of hollow tubular shafts or pipes 314 are adapted to fluidly connect vapor outlet 306 to the catheter, described herein.

Figure 4B:
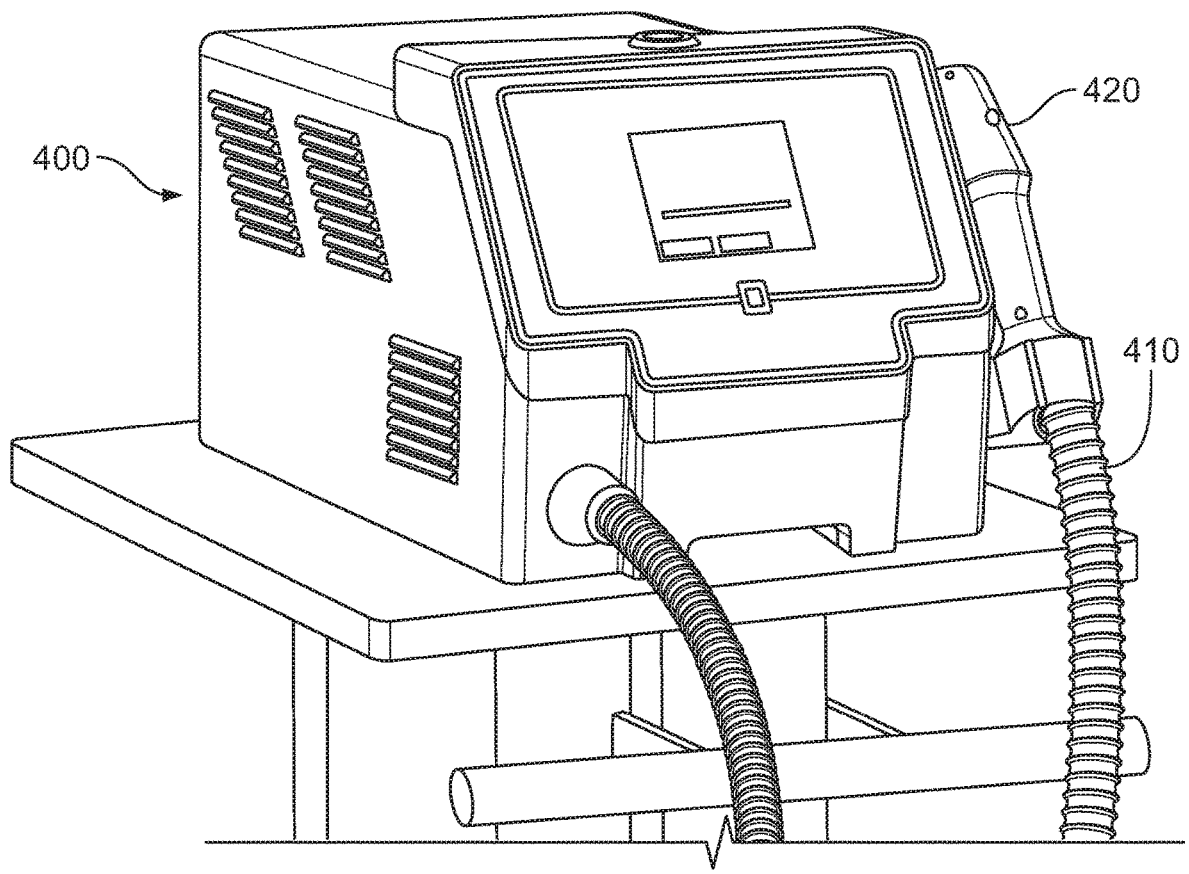

With reference to FIG. 4B, in embodiments, a flexible hollow tube or umbilical-like cord 410 extends from the generator 400 and terminates in a handle (420). The handle is adapted to operatively couple to an energy delivery catheter 440 via a hub assembly (such as hub assembly 450 shown in FIG. 5 and discussed herein). In embodiments, the hub assembly 450 or other connecting means is configured to allow for a secure, fluidly sealed, and quick release between the catheter 440 and generator handle 420. Examples of suitable quick connect and release mechanisms include, without limitation, Luer Lock hub assemblies and fittings.

In embodiments, a catheter and vapor generator are configured to be directly coupled to one another via mating connectors. Vapor delivery is controlled by the generator, a controller external to the generator, or actuating buttons and mechanisms on the catheter itself. For example, the catheter may comprise a handpiece portion to control vapor doses.

Although the vapor generator is described above having various specific features, the components and configurations of the vapor generator and catheter systems may vary. Additional vapor ablation systems are described in, for example, U.S. Patent Publication No. 2015/0094607 to Barry et al., and Pat. No. 7,913,698 to Barry et al., and Pat. No. 8,322,335 to Barry et al., and Pat. No. 7,993,323 to Barry et al.

In other embodiments, a condensable vapor is created in the handle portion of the catheter system. Consequently, a separate vapor generator unit is not required. Systems including a resistive heater are described in, for example, U.S. Patent Publication No. 2016/0220297 to Kroon et al., U.S. Patent Publication No. 2014/0276713 to Hoey et al., and U.S. patent application Ser. No. 16/203,541, filed Nov. 28, 2018, and entitled "VAPOR ABLATION HANDPIECE". Indeed, embodiments of the invention include a wide range of mechanisms to create and transport vapor through the working catheter as described herein.

Vapor Ablation Catheter

Figure 5:
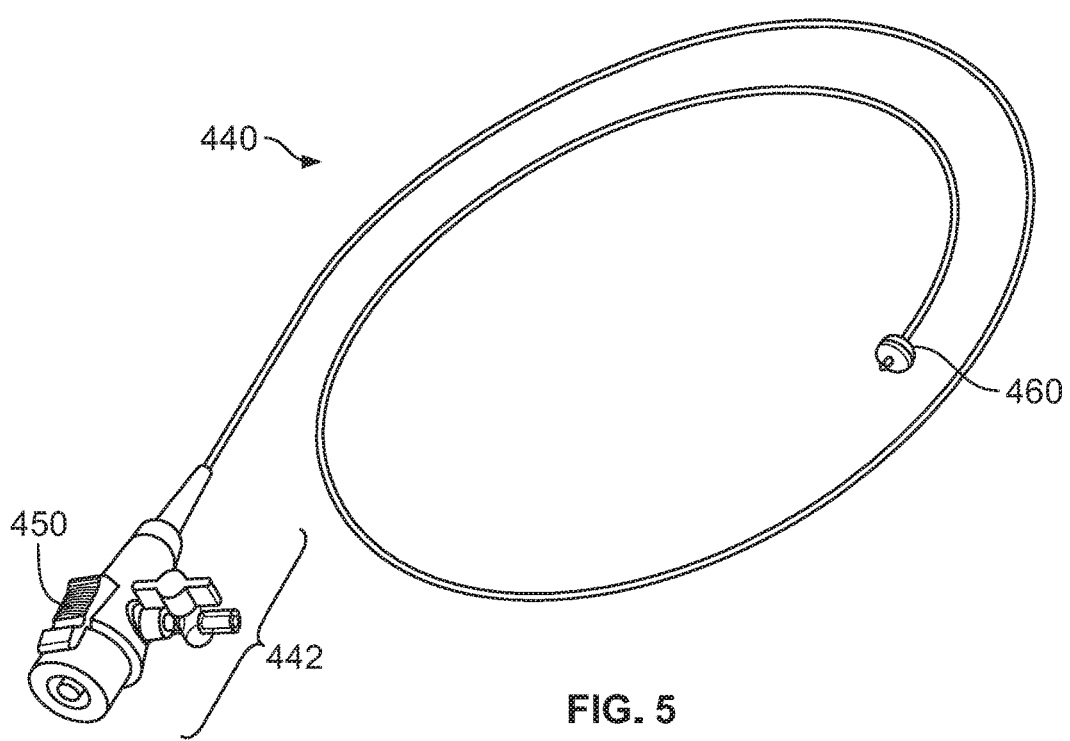

FIG. 5 illustrates a vapor ablation catheter 440 in accordance with one embodiment of the invention. Catheter 440 is shown having a proximal section 442, a distal end section 460, and intermediate section therebetween. Proximal section 442 is shown with hub 450 which may be connected to the generator as described above. Intermediate section is flexible and continues to distal end section 460. Examples of suitable materials for the catheter shaft include polyimide, PEBAX, silicone, PEEK, and stainless-steel braiding.

Figure 6:
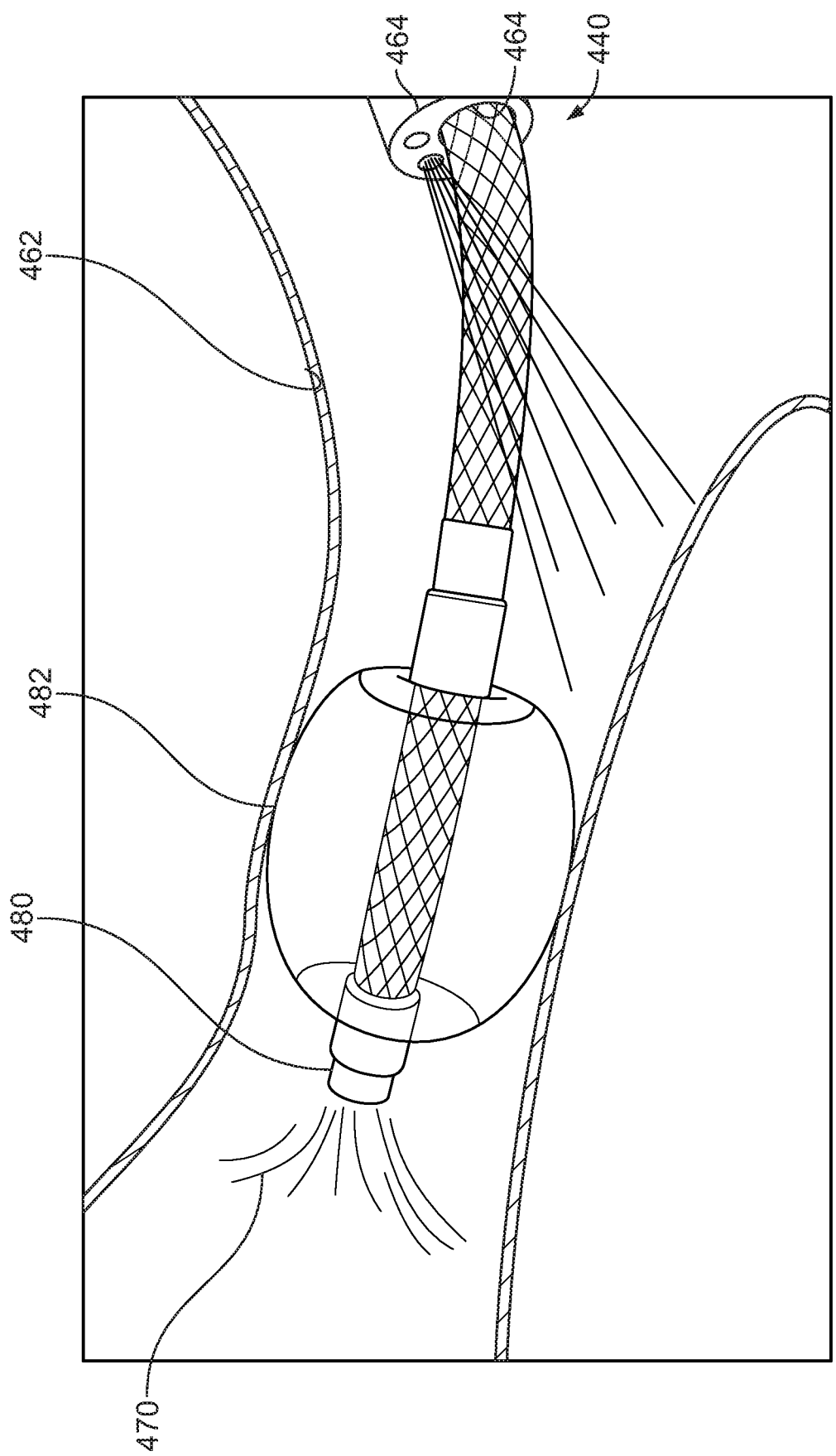

FIG. 6 is an enlarged view of the distal section 460 of vapor ablation catheter 440 in an airway 462. The catheter is shown extending from a working channel of a bronchoscope 464. Light from the bronchoscope illuminates the airway lumen.

Vapor 470 is shown being emitted from an axially-aimed distal port 480 towards the target section of the airway. The catheter 440 also includes an isolation member 482 to isolate the vapor 470 to the target tissue. The isolation member is visually transparent, allowing the physician to see through the member. Examples of isolation members include, without limitation, inflatable members, balloons, and expandable members.

Figure 7A:
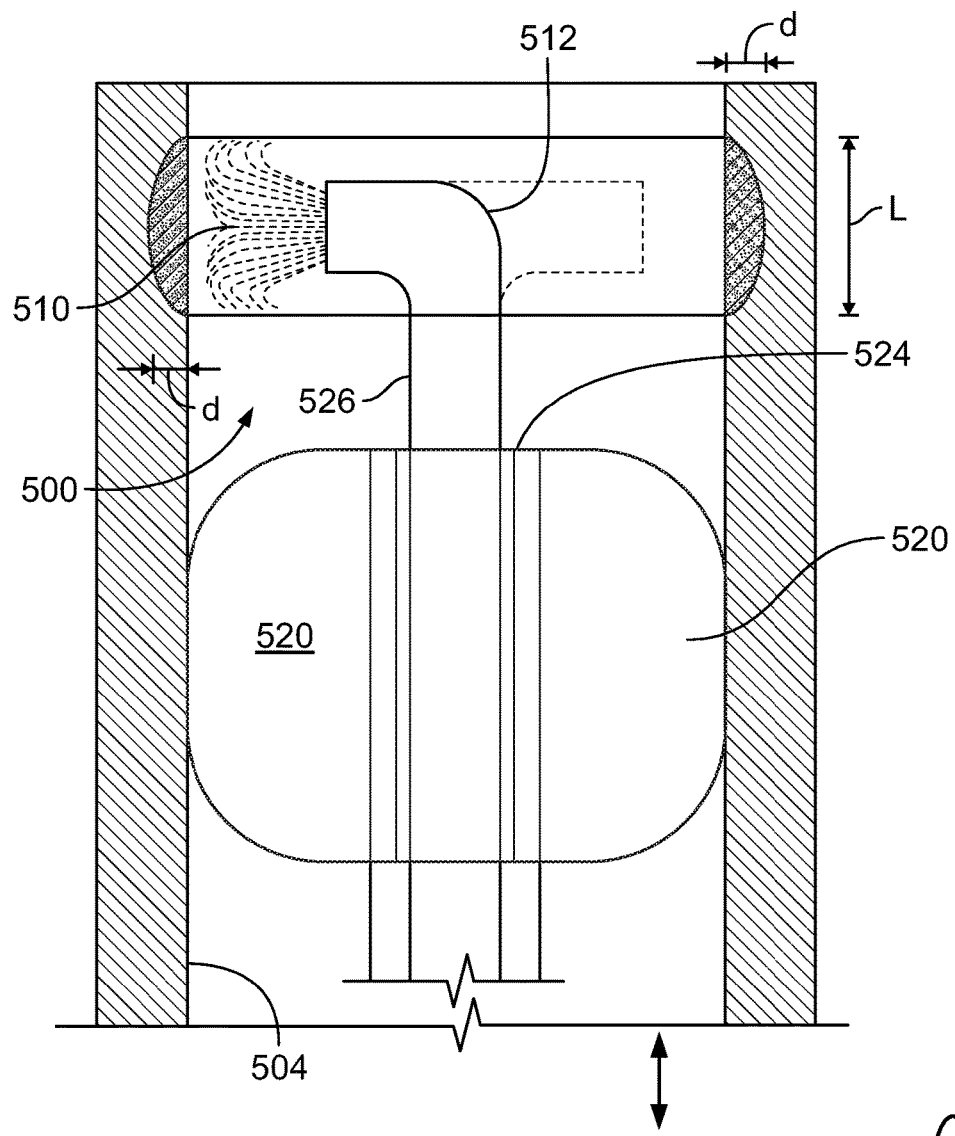

FIG. 7A shows an enlarged view of a distal section of another catheter 500 in an airway 504 delivering vapor 510. Unlike the catheter 440 discussed above, catheter 500 aims the vapor 510 directly towards the airway wall 504. The flowpath of the vapor is perpendicular to the airway wall. The distal section of the catheter 500 features a bend 512 ranging from 60 to 120 degrees, and preferably about 80-100 degrees, and most preferably about 90 degrees.

An isolation member 520 holds the catheter in place while emitting vapor and isolates the vapor to the target region. Additionally, in embodiments, the isolation member 520 includes a coupler 524, allowing the shaft 526 of the catheter to rotate relative to the isolation member. An example of a coupling mechanism is a tubular passageway through which the shaft 526 of the vapor catheter extends therethrough. Preferably, the components cooperate with one another to be fluidly sealed but axially and rotatably movable. In embodiments, an O-ring or gasket (e.g., a Teflon O-ring) is provided to facilitate a seal and permit motion between the components.

Figure 7B:
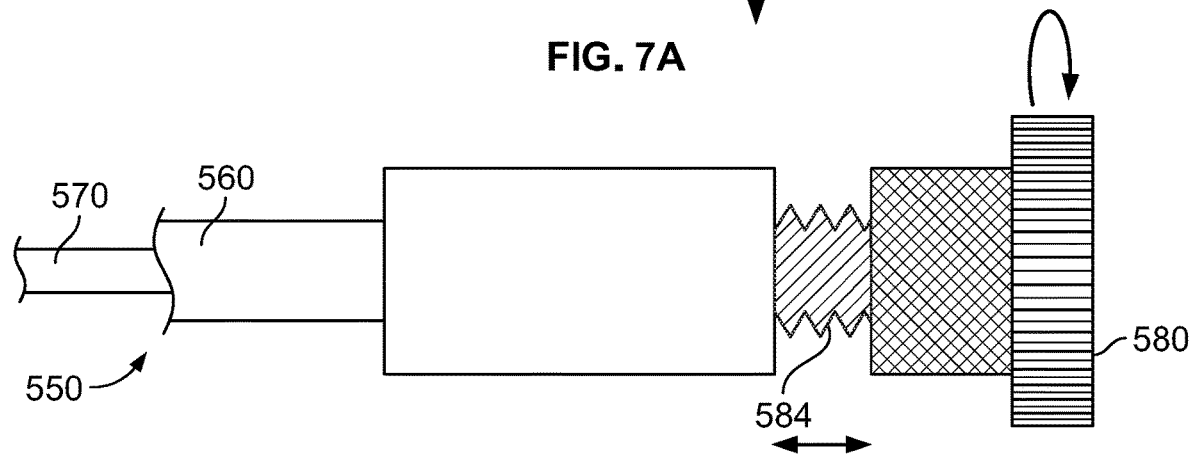

With reference to FIG. 7B, a handle 550 is shown that enables the physician to rotate the tip of the catheter to create a band-shaped ablation zone. Particularly, in the embodiment shown in FIG. 7B, handle 550 of catheter includes a hub 560 to which the isolation member 520 is connected. The vapor delivery shaft 570 is axially moveable within the hub assembly 560. Additionally, a knob 580 is connected to a proximal end of the vapor catheter to allow the physician to conveniently rotate and axially move the catheter relative to the balloon.

Rotation may be clock-wise or counter clockwise. Example rotation angles are between 0 and 180, up to 360 or more. Additionally, the physician may axially advance the catheter in combination with rotation to generate an elongated tubular ablation zone along the surface of the airway.

The incremental or controlled movement may be accomplished via a shaft advancement means. In embodiments, the hub assembly 560 includes a threaded shaft 584 to allow for incrementally advancing and rotating of the shaft relative to the balloon. As a result of this motion, the catheter can create a circumferentially complete band ranging from 5 to 20 mm in width (w).

Depth (d)

The depth (d) of the ablation lesion may also be controlled. In embodiments, the physician controls ablation parameters for the vapor delivery to limit the depth (d) of ablation to less than 1 mm, and in embodiments, between 0.3 and 0.7 mm, and preferably less than 0.5 mm into the wall. In embodiments, the parameters include but are not limited to vapor temperature, flowrate, and duration of vapor delivery. Non-limiting exemplary time durations to limit the ablation depth (d) to the above desired depths is less than 1 minute, less than 30 seconds, and less than 10 seconds. Exemplary non-limiting temperatures range from that described above to more preferably less than 100 degrees C. In embodiments, the duration of vapor delivery and temperature are adjusted to ablate the upper layer of the epithelium including the goblet cells, or top layer of the epithelium, and to let the underling tissue architecture remain intact. In embodiments, the time and temperature are set as described above to treat only the epithelium cell layers discussed above yet not damage deeper layers.

The depth of thermal ablation can also be controlled by a pulsing or duty cycle application of the vapor. Pulsing allows for the limited vapor dispersed to condense and be followed by a brief cooling period which will slow penetration of the steam energy. Alternating steam and cooling gas application to the wall can provide a fine/precise depth of penetration. A 10% duty cycle (10 parts steam followed by 90 parts cooling) will result in a shallower penetration of the ablation than a 50% duty cycle. A controlled solenoid and valve mechanism (similar to a fuel injector) could be programed to alternate gasses and achieve this duty cycle. Where a slow and more precise ablation is desired, the physician may opt for a lower duty cycle under 50%, or perhaps from 10 to 20%. On the other hand, for a deeper ablation zone, the physician may opt for a higher duty cycle. In embodiments, the higher or fast ablation duty cycle may range from 70 to 100%.

The depth of penetration can be monitored via observation and color change of the bronchial wall via an optical comparator system. Without intending to being bound by theory, as vapor is applied to the bronchial surfaces, the pink coloration of the lumen will change from pink to white in a progressive fashion from all pink to all white, where partial ablation is a mix of pink and white coloration. With this color change a correlation can be established between the coloration and the depth of penetration. As all airways are not the exact hue of pink, one could similarly monitor the change from the original color to be correlated to the energy delivered and depth of penetration.

The measure (or computation) of color change could be performed by an optical comparator system capable of graphic processing of the color vs a known color scale. An example of a suitable optical assessment technology is BLD Blood Leak Detector, manufactured by Sonotec US Inc. (Islandia, N.Y.) or the TT Electronics Photologic V OPB9000 reflective optical sensor, manufactured by TT Electronics (Boston, Mass.). With such an optical quality assessment of hue and difference from baseline, a system and method could be controlled by a feedback loop which would stop the application of vapor when the color change desired (e.g., a threshold hue change) had been verified, therefore achieving the desired depth of penetration. In embodiments, the vapor emission is halted when the real-time color change of the surface of the airway reaches a predetermined threshold color change.

The duty cycle for vapor ablation may also be adjusted (or varied) during a procedure. A high duty cycle could be applied to start to speed initial growth of the ablation depth. With significant Hue change as assessed by the optical comparator system, the duty cycle could be reduced (e.g., reduced by 10-25, 50 or in some embodiments 75%) to slow the growth of the depth of penetration and arrive asymptotic to the desired depth of penetration/hue for a precise control.

Figure 8A:
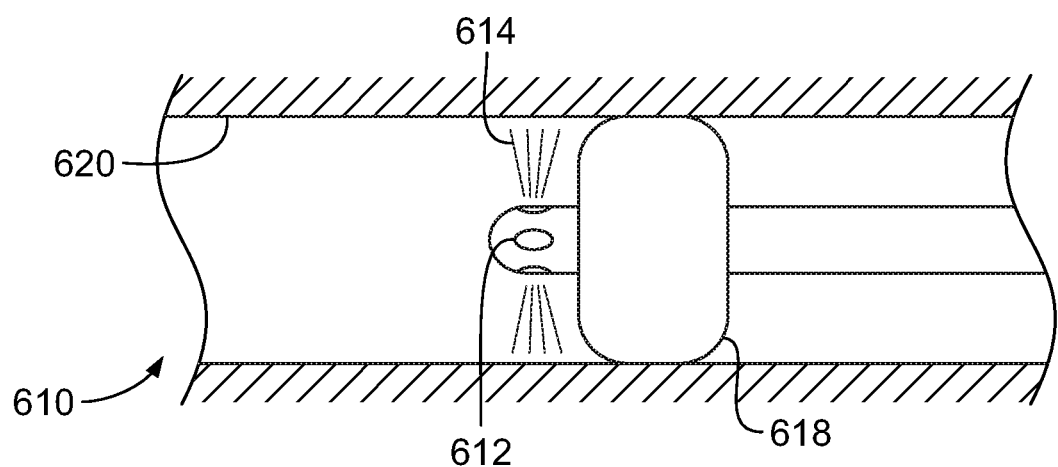

FIG. 8A shows the distal section of another vapor ablation catheter 610. Vapor ablation catheter 610 is similar to the vapor catheter described above except it features a laterally disposed egress port 612. Vapor 614 is aimed directly at the airway wall 620. Isolation member 618 secures the catheter in place, blocks the vapor from passing, and isolates a target section of the airway to be ablated distal to the isolation member.

Figure 8B:
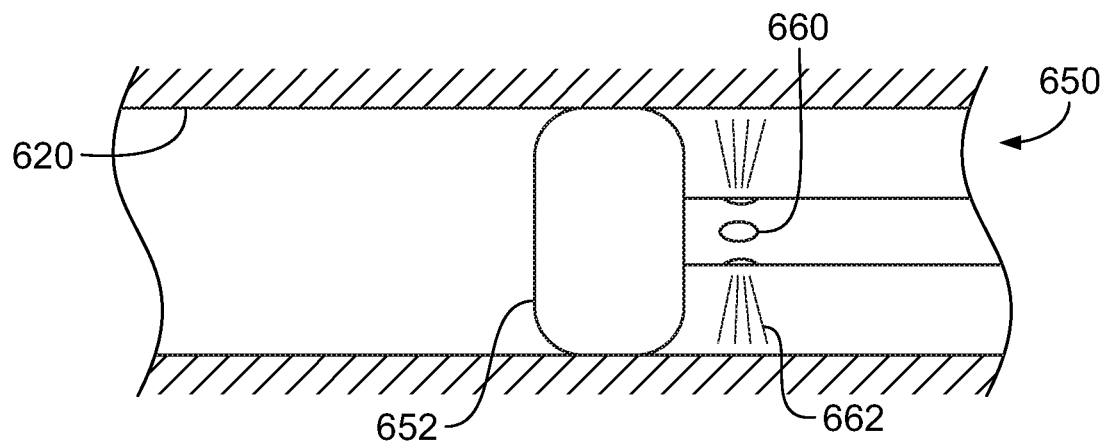

FIG. 8B shows the distal section of another vapor ablation catheter 650. Vapor ablation catheter 650 is similar to the vapor catheter 610 described above except that it features an isolation member 652 distal to the egress port 660. Vapor 662 is shown aimed at the airway wall 620 but the vapor is prohibited by the isolation member 652 from flowing distally into more remote airways not shown.

Figure 8C:
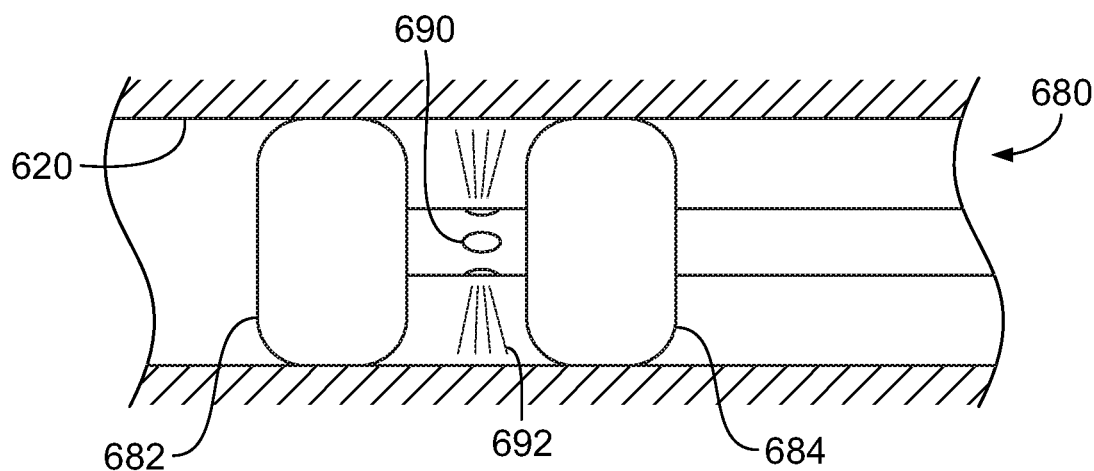

FIG. 8C shows the distal section of another vapor ablation catheter 680. Vapor ablation catheter 680 is similar to the vapor catheters 610, 650 described above except that it features two isolation members 682, 684. Isolation members 682, 684 are distal and proximal to the egress port(s) 690, respectively. In a sense, the isolation members and catheter have a dumbbell shaped configuration.

Vapor 692 is shown aimed at the airway wall 620 and is limited to the volume defined between the isolation members 682, 684 and the airway wall 620. In this manner, collateral damage to non-target tissues and airways is prohibited.

Figure 9:
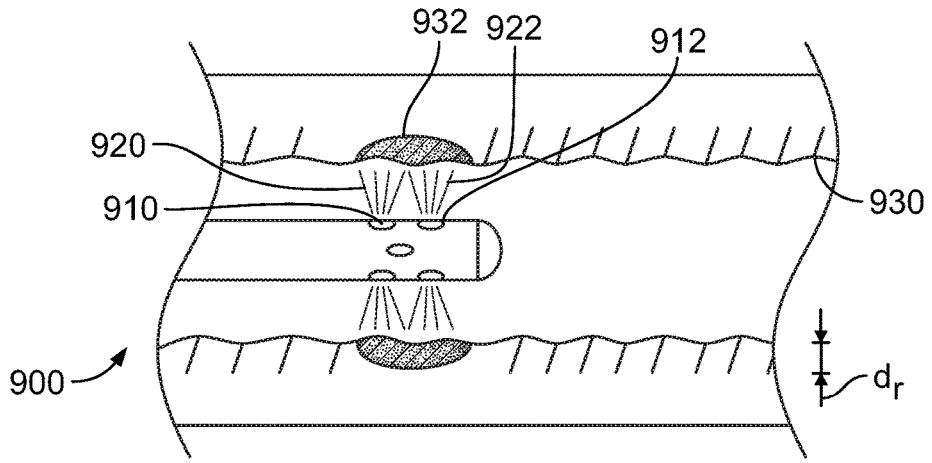

FIG. 9 shows a distal section of another vapor delivery catheter 900. Vapor ablation catheter 900 is similar to the vapor catheters described above except it features a plurality of laterally and circumferentially disposed egress ports 910, 912, etc. for the vapor 920, 922 to be aimed towards the airway wall 930 to create a complete continuous ring of ablation 932.

The ports 910, 912, etc. are shown in a group. Adjacent ports are spaced from one another such that the vapor flowpath (as the vapor flows into the wall) from one port overlaps with the vapor flowpath from an adjacent port. In embodiments, the distance (center to center) between the adjacent ports ranges from 0.5 to 5 mm.

The number of egress ports 910, 912, etc. may vary widely and range from 1-20, and more preferably 6-12. Additionally, the shape and size of the egress ports may vary. In embodiments, the egress port has a circular shape and a diameter in the range of 0.1 to 2 mm.

Optionally, although not shown, an isolation member may be disposed proximally, distally, or both proximally and distally to the group of egress ports.

Figure 10:
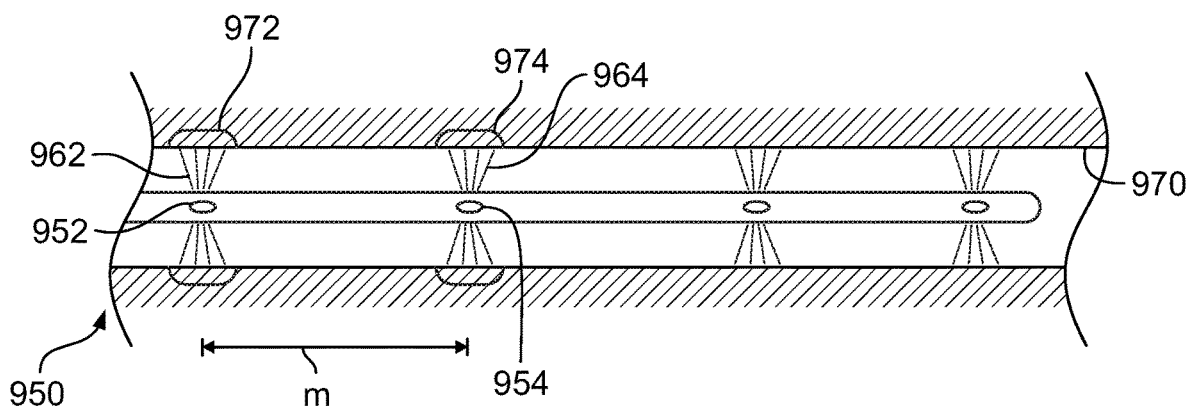
Figure 11:
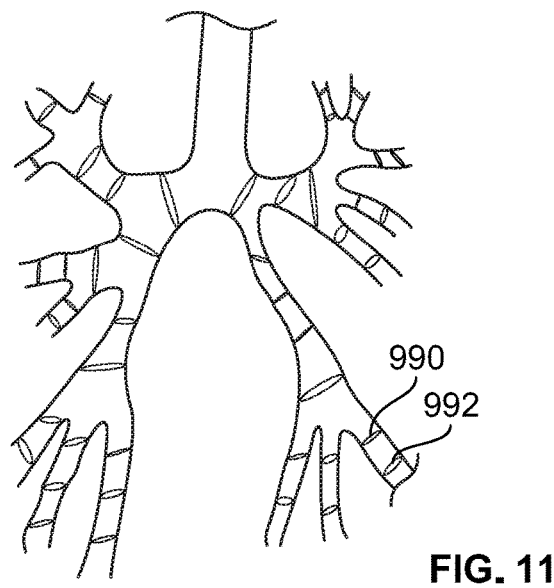

FIG. 10 shows a distal section of another vapor delivery catheter 950. Vapor ablation catheter 950 is similar to the vapor catheter described above in connection with FIG. 9 except it features an axially-offset (or spaced) configuration of egress ports 952, 954, etc. for the vapor 962, 964 to be aimed towards the airway wall 970 to create a set or chain of spaced-apart rings of ablation 972, 974. Adjacent ports 952, 954 can be spaced apart a predetermined distance (m) to generate preplanned ablation pattern such as the pattern shown in FIG. 11 wherein adjacent rings 990, 992, etc. are offset from one another a predetermined distance (m). In embodiments, the predetermined distance (m) ranges from 4 to 15 mm.

Also, the number of discrete groups of ports may vary from that shown in FIG. 10 (namely, 4 spaced apart groups). In embodiments, the number of spaced apart groups ranges from 2-8, more preferably 2-6, and most preferably from 2-4.

Additional examples of vapor delivery catheter configurations are described in the literature. Another example of a vapor catheter having components and structures which may be combined with the subject invention is described in U.S. Pat. No. 8,444,636 to Shadduck and Hoey; and U.S. Patent Publication No. 2014/0025057 to Hoey and Shadduck. The catheter and tip configuration may vary widely and the invention is only intended to be limited as recited in the appended claims.

Chronic Bronchitis or Asthma Treatment Method

Figure 12:
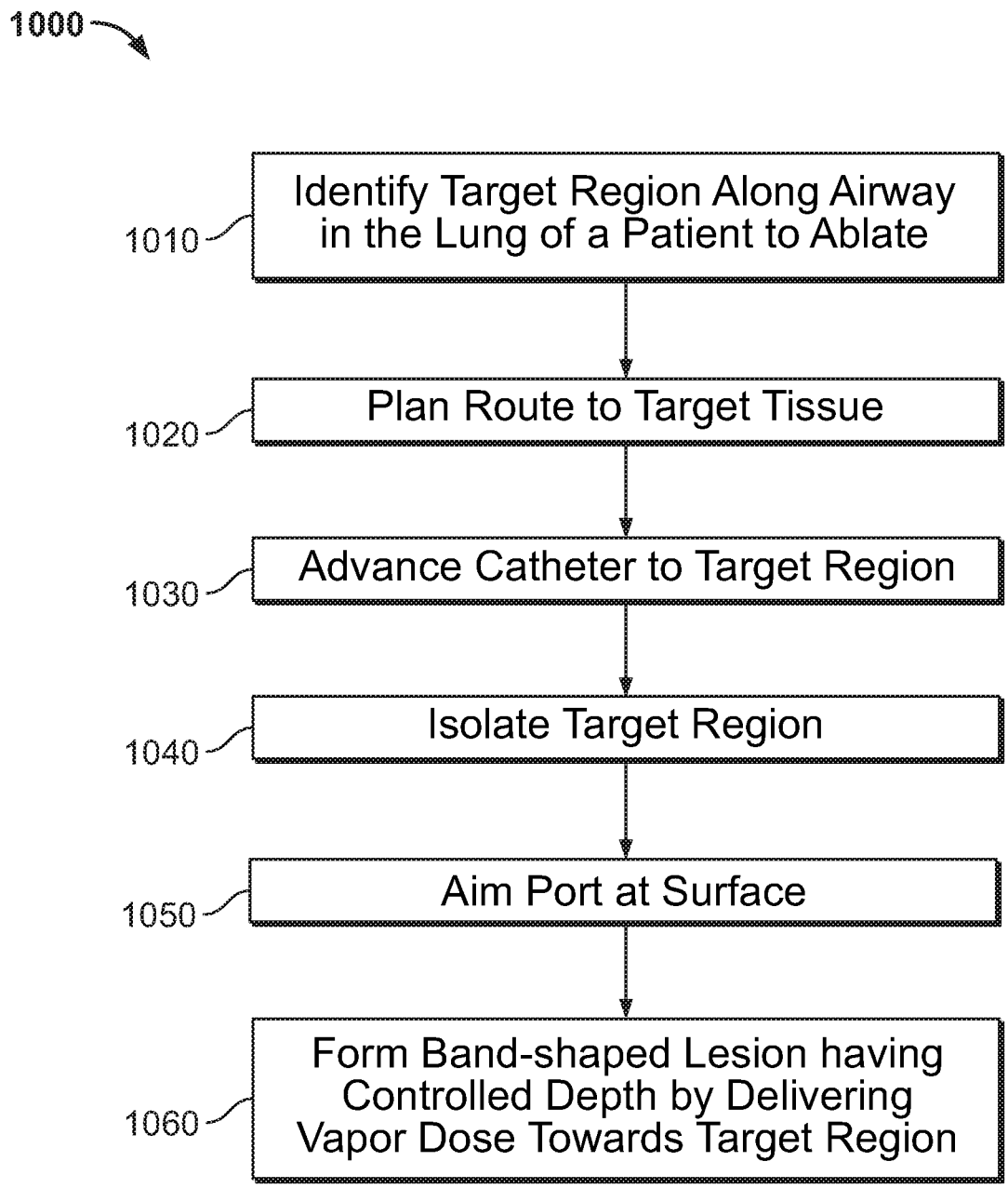

FIG. 12 is a flowchart illustrating a method 1000 for the treatment of obstructive lung and/or inflammatory disease such as chronic bronchitis and asthma.

Step 1010 states to identify the target region along an airway in the lung of a patient to ablate. An example of a candidate region to ablate may be a portion along the trachea, main bronchus, bronchioles from 1 generation up to the 5 generation. Endoscopy or noninvasive means such as MRI may be applied to view and identify the target.

Step 1020 states to plan route to the target tissue. Optionally, planning software is employed to visualize the target region in renderings of the patient's lungs (e.g. a 3D reconstruction of the airway tree based on a patient's CT or MRI image data). Examples of route planning techniques are described in U.S. Pat. No. 9,037,215 and U.S. Patent Publication No. 2009/0156895, both to Higgins et al. See also the LungPoint® Planner, manufactured by Broncus Medical, Inc., (San Jose, Calif.).

Step 1030 states to advance the catheter to the target tissue. As described above, the physician may advance the catheter through the working channel of a scope to the target region.

Step 1040 states to isolate the target region. In embodiments, this step is performed as described above by inflating or expanding one or more isolation members to limit the vapor to the target region or section of airway.

Step 1050 states to aim an egress port of the catheter at the surface of the airway wall. Aiming may be performed as described above by rotation of the port, movement of the port axially, or providing multiple ports circumferentially or axially along the shaft of the catheter.

Optionally, the distance between the airway wall and the port is adjusted by, e.g., switching out another catheter having a different diameter shaft to position each of the egress ports closer or farther from the airway wall.

In embodiments, a method further comprises controlling or adjusting the distance from the egress port to the surface of the airway based on a target depth to be achieved by the emitted vapor.

Step 1060 states to deliver a vapor dose towards the target. As described herein, the vapor dose is controlled by various ablation parameters to provide an amount of energy to the target region to cause necrosis to a depth as described herein, and in particular embodiments, such that only the top layer of the epithelium is ablated. In embodiments, the ablation parameters are controlled such that the vapor dose ranges from 100 to 1000 calories. The amount of energy can be controlled by time duration, flow rate, temperature, duty cycle, and vapor quality.

Alternative Embodiments

The invention has been discussed in terms of certain embodiments. One of skill in the art, however, will recognize that various modifications may be made without departing from the scope of the invention. For example, numerous variations, changes, and substitutions will now occur to those skilled in the art without departing from the invention. For example, in embodiments, lesions may be created by the vapor systems described above which form non-band shaped lesions on the airway. Lesions may be sprayed/painted on epithelium of the airway in a non-contiguous manner, in patches, segments, half rings, arcuate segments, etc., and the control parameters can be used to limit the depth of the lesion to the target depth, preferably less than 1 mm so as to leave the underlying tissue architecture intact. Moreover, while certain features may be shown or discussed in relation to a particular embodiment, such individual features may be used on the various other embodiments of the invention.

The invention claimed is:

1. An intraluminal or bronchoscopic method for treating obstructive lung disease comprising:
   determining at least one discrete band-shaped area along a surface of an airway to ablate to form a band-shaped lesion having a width and a depth;
   computing a dose of vapor to aim at the surface of the airway to form the band-shaped lesion based on a set of ablation parameters, the set of ablation parameters selected from the group consisting of (a) anatomic, (b) device and controller, and (c) treatment-specific parameters;
   advancing a vapor ablation catheter into the airway of a patient lung and aiming at least one egress port of the vapor ablation catheter directly towards the surface of the airway; and
   delivering vapor from the at least one egress port into the surface of the airway and according to said computed dose of vapor, thereby causing formation of the band-shaped lesion wherein the dose of vapor from the computing step is predetermined to cause the band-shaped lesion to have a depth in the range from 0.1 to 0.7 mm, and a width in the range from 5 to 20 mm.

2. The method of claim 1, further comprising rotating the at least one egress port during the delivering step to form the band-shaped lesion.

3. The method of claim 1, wherein the vapor ablation catheter comprises a catheter shaft, and the at least one egress port comprises a plurality of egress ports arranged about the circumference of the catheter shaft, such that the vapor is directed radially in multiple directions towards the surface of an airway wall from the catheter shaft.

4. The method of claim 1, wherein the at least one egress port comprises a plurality of egress ports axially spaced from one another at a distance (d).

5. The method of claim 4, wherein the distance (d) is equal to or greater than 1 mm.

6. The method of claim 1, wherein the step of delivering comprises pulsing according to a varying duty cycle.

7. The method of claim 6, further comprising measuring the depth of the band-shaped lesion.

8. The method of claim 7, wherein the duty cycle is adjusted based on the measured depth of the band-shaped lesion.

9. The method of claim 8, wherein the duty cycle commences at a first range, and is adjusted to a second range, and the second range is less than the first range.

10. The method of claim 9, wherein the first range is from 70 to 100%, and the second range is under 50%.

11. The method of claim 1, further comprising isolating a region of the airway from the at least one egress port.

12. The method of claim 11, wherein the isolating is performed using at least one inflatable member.

13. The method of claim 1, wherein a set of ablation parameters comprises time duration, and the time duration ranges from 3 to 30 seconds.

14. The method of claim 13, further comprising controlling a distance from the at least one egress port to an airway wall, and wherein the distance is in the range of 1 to 5 mm.

15. An intra-airway method for treating obstructive lung disease in a patient comprising:
advancing a vapor ablation catheter into an airway of a patient lung;
isolating a target section along the airway to ablate;
aiming at least one egress port of the vapor ablation catheter directly towards a surface of an airway wall of the airway within the target section;
emitting vapor from the at least one egress port into the surface of the airway wall causing a thin ablation layer to form extending from the surface of the airway wall to a depth in the airway wall;
visually monitoring the surface of the airway wall and computing a real-time hue change as the ablation layer is forming; and
controlling the depth of the ablation layer to include the epithelial layer and exclude the smooth muscle layer of the airway wall.

16. The method of claim 15, wherein the isolating is performed using a balloon.

17. The method of claim 16, wherein the at least one egress port comprises a first set of egress ports circumferentially spaced around a shaft of the vapor ablation catheter.

18. The method of claim 17, wherein the vapor ablation catheter comprises a second set of circumferentially disposed egress ports, the second set spaced a distance from the first set wherein the distance is at least 4 mm.

19. The method of claim 15, wherein the controlling step comprises controlling a time duration of ablation, and the time duration ranges from 3 to 30 seconds.

20. The method of claim 15, wherein the controlling step comprises controlling a distance from the at least one egress port to the airway wall, and wherein the distance is in the range of 1 to 5 mm.

21. The method of claim 15, further comprising controlling or setting an ablation control parameter selected from the group consisting of time duration, duty cycle, energy rate, flowrate, temperature, and pressure.

22. The method of claim 15, further comprising controlling or adjusting a distance from the at least one egress port to the surface of the airway wall based on a target depth to be achieved by the emitted vapor.

23. The method of claim 15, wherein the step of controlling the depth of the ablation layer comprises halting the emitting vapor if the real-time hue change reaches a predetermined threshold hue level change.

\* \* \* \* \*